US008534134B2

(12) United States Patent
Buehler et al.

(10) Patent No.: US 8,534,134 B2
(45) Date of Patent: Sep. 17, 2013

(54) MECHANICAL LOAD TESTING SYSTEM AND PRESSURE APPLICATOR FOR A PHOTOVOLTAIC DEVICE

(75) Inventors: Pat Buehler, Pemberville, OH (US); David Kahle, Monclova, OH (US); Kevin Niebel, Toledo, OH (US); Geoffrey Dean Rich, Bowling Green, OH (US)

(73) Assignee: First Solar, Inc., Perrysburg, OH (US)

( * ) Notice: Subject to any disclaimer, the term of this patent is extended or adjusted under 35 U.S.C. 154(b) by 207 days.

(21) Appl. No.: 13/112,113

(22) Filed: May 20, 2011

(65) Prior Publication Data
US 2011/0283806 A1    Nov. 24, 2011

Related U.S. Application Data

(60) Provisional application No. 61/346,608, filed on May 20, 2010.

(51) Int. Cl.
*G01N 3/00* (2006.01)
(52) U.S. Cl.
USPC ............................................. 73/798; 73/760
(58) Field of Classification Search
USPC ................. 73/760, 797, 816, 820, 798
See application file for complete search history.

(56) References Cited

U.S. PATENT DOCUMENTS

| | | | |
|---|---|---|---|
| 3,286,516 A | | 11/1966 | Post |
| 3,788,231 A | * | 1/1974 | Bloomfield ................. 104/23.2 |
| 4,589,288 A | | 5/1986 | Porter et al. |
| 5,060,516 A | | 10/1991 | Lau et al. |
| 5,524,636 A | * | 6/1996 | Sarvazyan et al. ............ 600/587 |
| 5,699,274 A | | 12/1997 | Starostovic |
| 5,915,673 A | * | 6/1999 | Kazerooni ..................... 254/270 |
| 6,055,867 A | | 5/2000 | Dunne et al. |
| 6,931,942 B2 | | 8/2005 | Uhlik et al. |
| 7,069,170 B2 | * | 6/2006 | Vines et al. .................... 702/138 |
| 7,201,064 B2 | | 4/2007 | Doak et al. |
| 7,293,519 B2 | * | 11/2007 | Montgomery et al. ..... 114/230.1 |
| 7,380,463 B2 | | 6/2008 | Escobar et al. |
| 7,581,451 B2 | | 9/2009 | Thompson et al. |
| 7,690,265 B2 | | 4/2010 | Cipra |
| 8,291,871 B2 | * | 10/2012 | Rabhi .......................... 123/48 B |
| 2008/0148863 A1 | | 6/2008 | Thompson et al. |
| 2009/0179651 A1 | | 7/2009 | Elgar et al. |
| 2010/0046575 A1 | | 2/2010 | Hebert et al. |
| 2010/0313637 A1 | | 12/2010 | Hsu et al. |

FOREIGN PATENT DOCUMENTS

| DE | 102008024406 | 11/2009 |
|---|---|---|
| JP | 2003194689 | 7/2003 |

* cited by examiner

*Primary Examiner* — Max Noori
(74) *Attorney, Agent, or Firm* — Dickstein Shapiro LLP

(57) ABSTRACT

A system for determining load capacity for a photovoltaic module includes a clip to position a photovoltaic module surface at a load test position and a load test device proximate to the clip, including a pressure applicator and an actuator, wherein the actuator is capable of moving the pressure applicator toward the load test position.

44 Claims, 4 Drawing Sheets

MECHANICAL LOAD TESTING SYSTEM AND PRESSURE APPLICATOR FOR A PHOTOVOLTAIC DEVICE

CROSS-REFERENCE TO RELATED APPLICATIONS

This application claims the benefit of U.S. Provisional Application No. 61/346,608, filed May 20, 2010, the entire disclosure of which is incorporated by reference herein.

TECHNICAL FIELD

The present invention relates to photovoltaic modules and methods of testing load capacity for same.

BACKGROUND

Photovoltaic modules can be load tested to ensure compliance with various industry standards. Past load testing methods and systems can present many shortcomings. For example, past methods and systems can be inefficient, inaccurate, time-consuming, and/or labor intensive.

DETAILED DESCRIPTION

Figure 1:
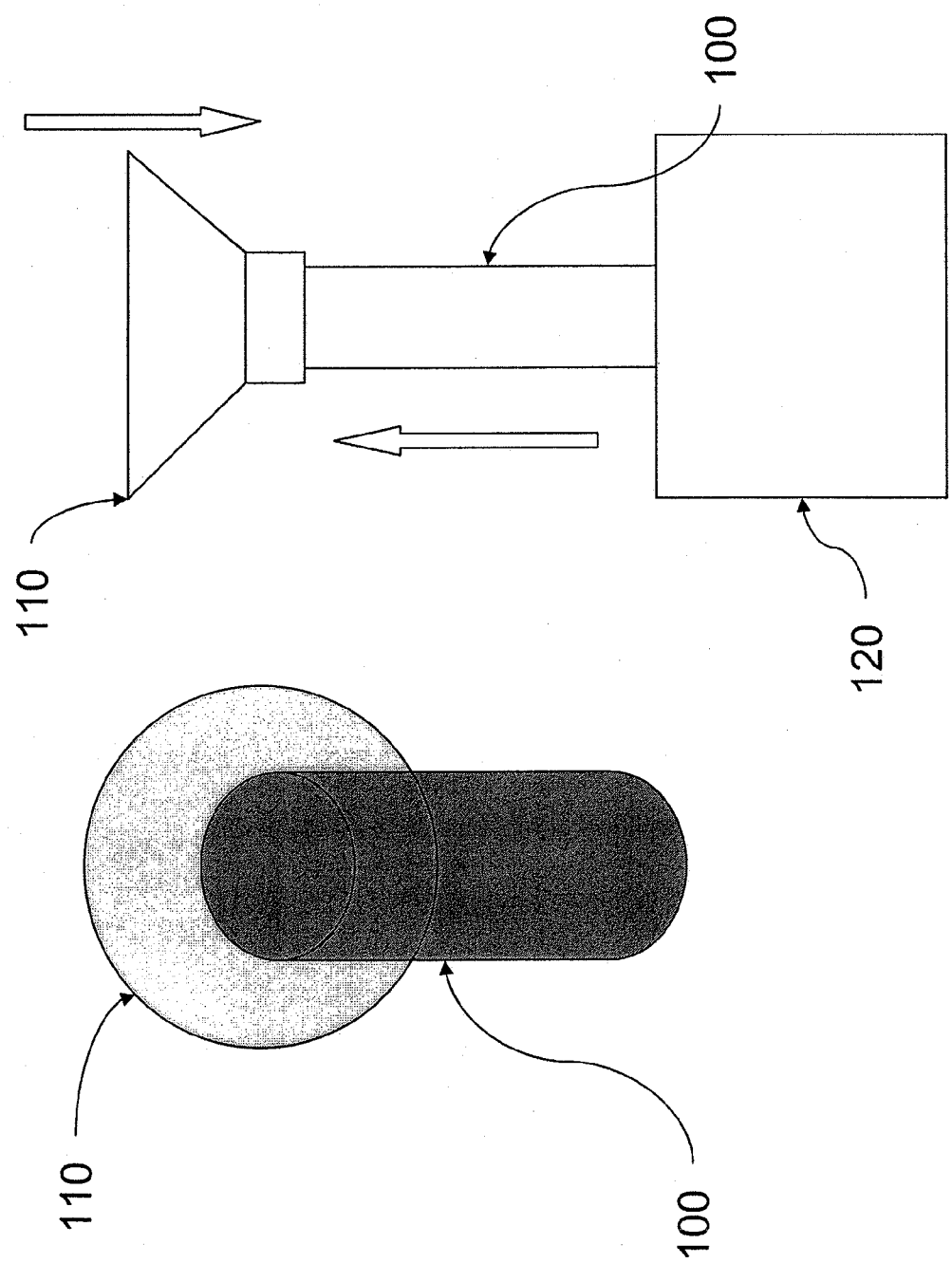
FIG. 1 is a schematic of an actuator, including a pressure applicator and a vacuum pump.

A photovoltaic module may undergo load testing to determine its ability to withstand various load forces in the field. Testing can be carried out to ensure compliance with industry standards, such as IEC 61646. Loads that are tested for can be attributable to any number of factors, including, for example, wind, snow, static, or ice. Existing methods of load testing involve manually loading the modules with lead- or water-filled bags. Such methods can be labor intensive and time-consuming. Furthermore, it can be difficult to load the bags to achieve a uniform load distribution.

In one aspect, a system for load testing a photovoltaic module can include a clip to position a photovoltaic module surface at a load test position and a load test device proximate to the clip. The load test device can include a pressure applicator and an actuator. The actuator can be capable of moving the pressure applicator toward the load test position. The actuator can be capable of moving the pressure applicator away from the load test position. The pressure applicator can include a suction cup. The pressure applicator can include a pad. The actuator can include a pneumatic actuator. The pneumatic actuator can include an air cylinder. The actuator can include a motor. The actuator can include a hydraulic cylinder. The load test device can include one or more additional pressure applicators connected to one or more additional respective actuators capable of moving their respective pressure applicators.

The system can include a controller capable of outputting a load signal to the load test device to apply pressure at the load test position. The pressure can include positive pressure applied to push a photovoltaic module surface from the load test position in a direction away from the load test device. The pressure can include negative pressure applied to pull a photovoltaic module surface from the load test position in a direction toward the load test device. The system can include a vacuum pump connected to the suction cup to connect the suction cup to a photovoltaic module surface. The system can include a load fail detector capable of detecting breakage in a photovoltaic module. The load fail detector can include an accelerometer attached to a photovoltaic module.

In one aspect, a system for determining load capacity for a photovoltaic module may include a chamber configured to receive a photovoltaic module. The system may include an array of air cylinders positioned proximate to the chamber. The system may include a plurality of suction cups. Each one of the plurality of suction cups may be connected to each air cylinder of the array of air cylinders. The system may include a vacuum pump connected to each suction cup to allow the suction cup to be secured to a surface of a photovoltaic module. The system may include an air pressure regulator in connection with the array of air cylinders. Each one of the array of air cylinders may be connected to a common manifold to ensure a substantially even distribution of air pressure. The system may include a controller in connection with the air pressure regulator. The air pressure regulator may be configured to apply pressure to a photovoltaic module received by the chamber.

The controller may be configured to output a load signal to the air pressure regulator. The load signal may define an amount of negative or positive pressure for the air pressure regulator to apply to a photovoltaic module via the array of air cylinders. The air pressure regulator may be configured to adjust a negative or positive pressure on a photovoltaic module, upon receiving the load signal from the controller. The system may include an accelerometer in connection with the controller. The accelerometer may be configured to determine formation of a crack in a photovoltaic module received by the chamber, and to output a threshold load signal to the controller. The threshold load signal may define a maximum sustainable load for a photovoltaic module received by the chamber. The controller may be configured to identify a threshold load capacity of a photovoltaic module received by the chamber. The system may include a power supply in connection with the air pressure control regulator. The system may include a temperature sensor in connection with the controller for determining a temperature within the chamber. The controller may be configured to output a temperature adjustment signal. The temperature adjustment signal may define a new chamber temperature. The controller may include a temperature control device configured to increase or decrease a temperature within the chamber. The array of air cylinders may be positioned within the chamber. The chamber may be configured to receive a photovoltaic module on top of the array of air cylinders. The chamber may include one or more clips for securing a photovoltaic module within the chamber.

A method for determining load capacity for a photovoltaic module may include positioning a photovoltaic module proximate to an array of air cylinders; applying a positive or negative air pressure to the photovoltaic module via the array of air cylinders; and identifying a threshold load capacity of the photovoltaic module. The threshold load capacity may define a maximum sustainable quantity of applied positive or negative pressure for the photovoltaic module.

The method may include adjusting the applied positive or negative pressure. The step of applying a positive or negative pressure may include applying positive air pressure to a surface of the photovoltaic module. The step of applying a positive or negative pressure may include applying a suction force to a surface of the photovoltaic module.

The method can include setting a first temperature in the chamber. The first temperature can be between about −20 degrees C. and about 140 degrees C. The method can include adjusting the first temperature to a second temperature. The second temperature can be between about −20 degrees C. and about 140 degrees C. The second temperature can be between about −10 degrees C. and about 110 degrees C. The second temperature can be more than about −20 degrees C. The second temperature can be more than about 40 degrees C. The second temperature can be more than about 80 degrees C. The second temperature can be less than about 100 degrees C. The second temperature can be less than about 140 degrees C. The method may include identifying a crack in the photovoltaic module caused by the applied positive or negative pressure. The identified threshold capacity may correspond to the applied positive or negative pressure that caused the crack in the photovoltaic module.

Figure 2:
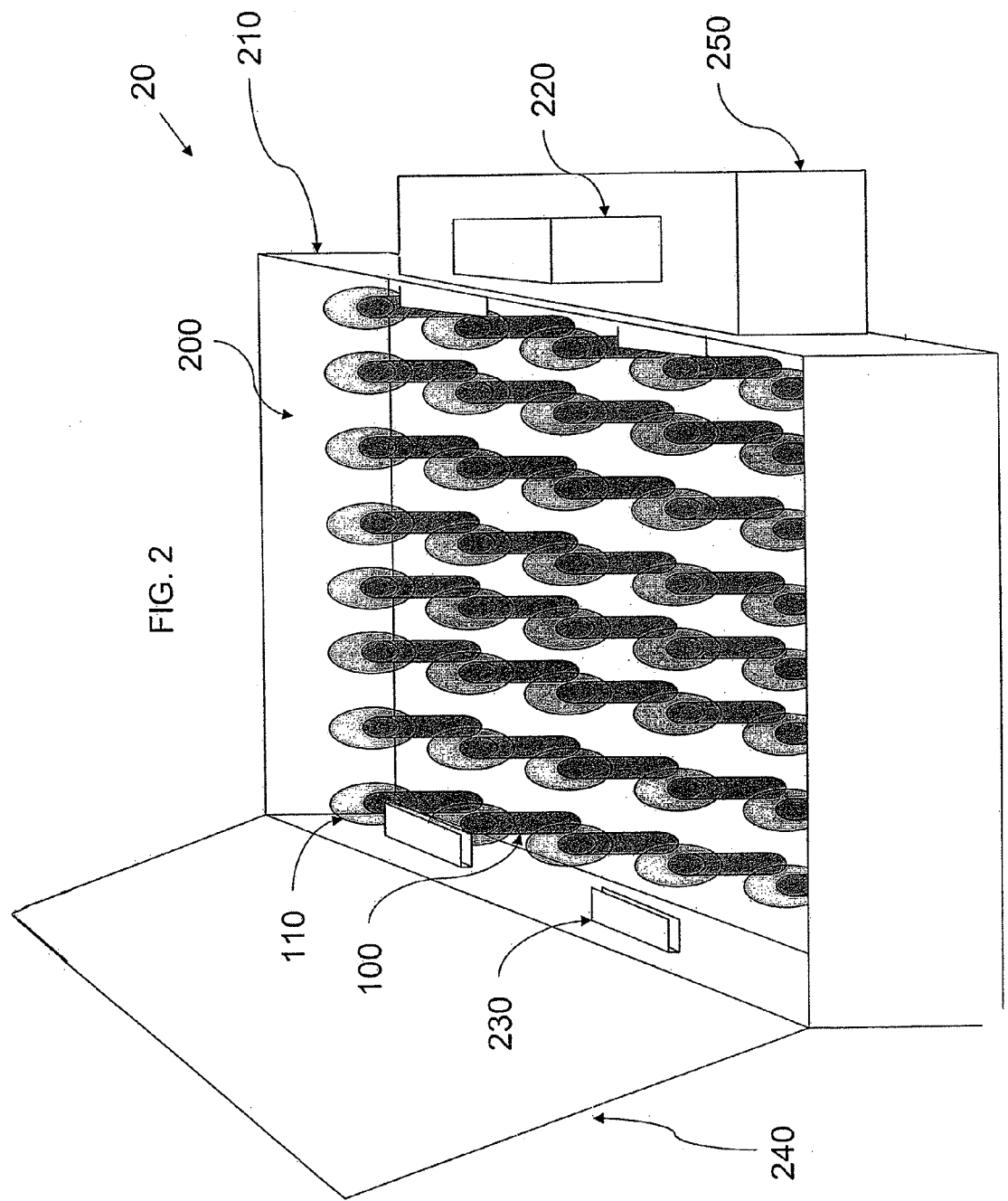
FIG. 2 is a schematic of a mechanical load testing system, including an array of air cylinders.

Referring now to FIG. 1, by way of example, a mechanical load system may include a load test device having one or more actuators 100 physically connected to pressure applicators 110. Actuator 100 can include any suitable actuator capable of physically moving pressure applicator 110 with respect to a photovoltaic module surface positioned by a clip at a load test position (e.g., toward or away from the load test position). Actuator 100 can include a pneumatic actuator such as an air cylinder. Actuator 100 can include a motor. Actuator 100 can include a hydraulic cylinder. Pressure applicator 110 can be any suitable implement for contacting and applying pressure to a photovoltaic module surface located at the load test position. Pressure applicator 110 can include a pad. Pressure applicator 110 can include a suction cup. Pressure applicator 110 can be formed of any suitable material, including metal, plastic, synthetic and/or natural fibers. Pressure applicator 110 can be integral to actuator 100.

Where pressure applicator 110 includes a suction cup, the load test device can include vacuum pump 120 attached to the suction cup. As a result, when the suction cup can contact and secure a photovoltaic module surface. Actuator 100 can be configured to move in alternate directions, for example, with respect to a load test position as indicated by the arrows in FIG. 1. The load test position can be defined, for example, by where a photovoltaic module is positioned by clips. Actuator 100 may be configured to apply a positive or negative pressure. Referring now to FIG. 2, a mechanical load system 20 may include a plurality of actuators 100 assembled in an array 200. Each actuator 100 of array 200 may be connected to a common manifold to ensure uniform distribution of positive or negative pressure applied by actuators 100. Array 200 may be connected to a pressure regulator 250 (e.g., an air pressure regulator where actuator 100 is an air cylinder), which may be connected to a controller 220. Controller 220, via pressure regulator 250, can be configured to provide positive or negative pressure through each actuator 100 of array 200. Controller 220 can be configured to adjust an applied positive or negative pressure at any suitable rate. For example, controller 220 may be configured with a predefined test procedure that simulates application of a certain load for a preset amount of time, and to adjust the load (at any suitable speed or frequency) consistent with the test procedure. For example, controller 220 may be configured to apply a predetermined load for a fixed duration, and then to simulate removal of that load for a predetermined amount of time; the load can then be reapplied periodically, to test the ability of the module to withstand periodic load quantities over time. Alternatively, controller 220 may be configured to gradually increase the load amount, to simulate the gradual accumulation of a substance (e.g., snow) on the module.

Figure 3:
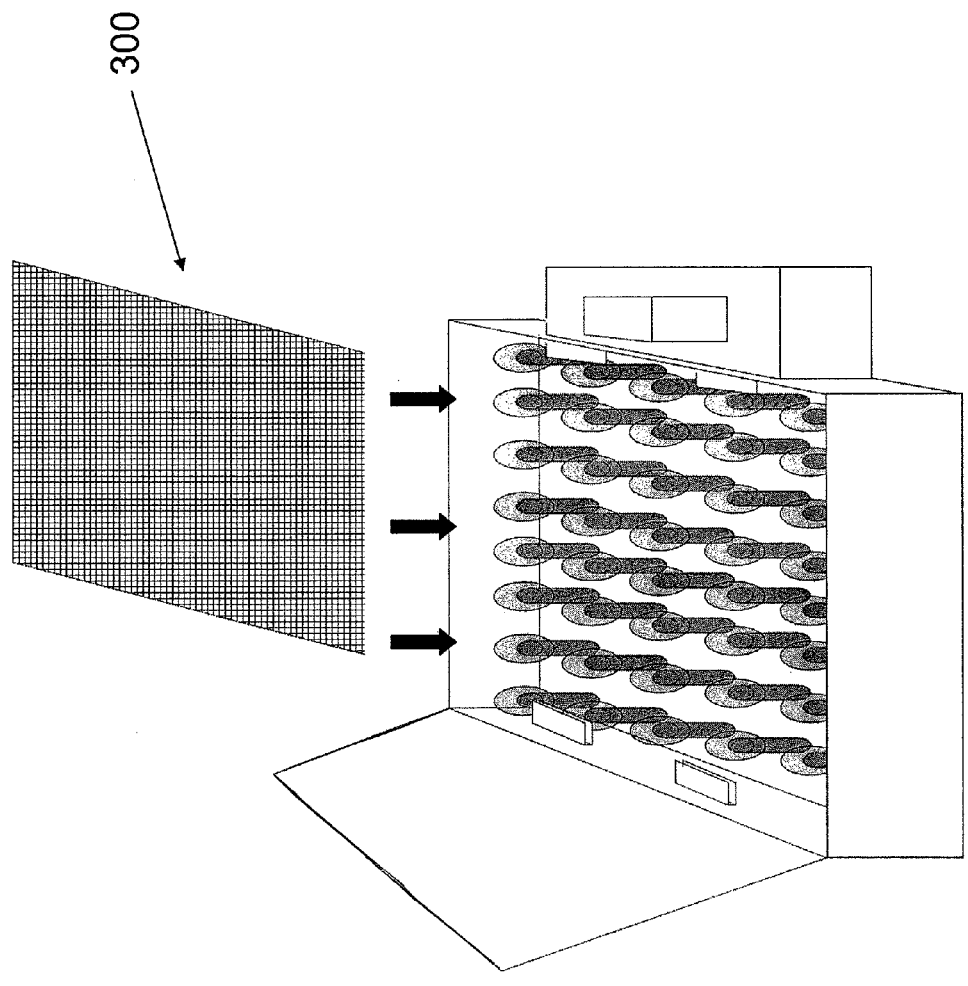
FIG. 3 is a schematic of a mechanical load testing system, including an array of air cylinders.
Figure 4:
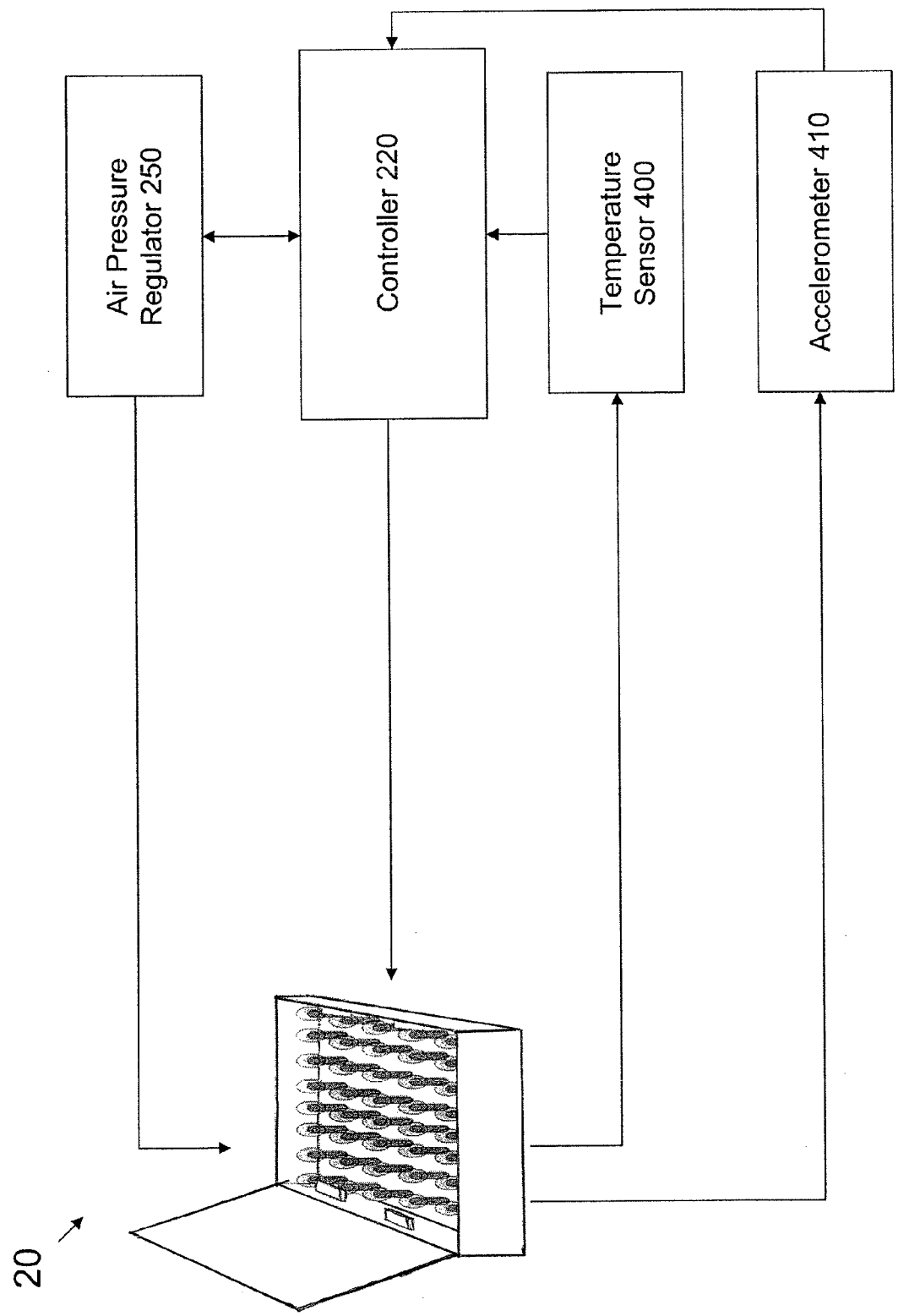
FIG. 4 is a schematic of a mechanical load testing system, including an array of air cylinders.

Referring to FIGS. 2 and 3, mechanical load system 20 may include a chamber 210 configured to receive a photovoltaic module 300. Chamber 210 may include one or more clips 230 configured to secure photovoltaic module 300 within the chamber 210. Chamber 210 may have a cover 240 to effectively seal photovoltaic module 300 within the chamber. Chamber 210 may have a temperature-controlled environment, which may be adjusted, using any suitable means, including, for example, controller 220. Chamber 210 may have any suitable temperature, including, for example, a temperature above about −40 degrees C., above about 0 degrees C., above about 40 degrees C., below about 120 degrees C., below about 80 degrees C., or below about 40 degrees C. The air temperature within chamber 210 may be set or adjusted (by controller 220, for example) to any suitable temperature. Referring to FIG. 4, system 20 may include a temperature sensor 400. Temperature sensor 400 may be located substantially proximate to chamber 210, for example, within chamber 210. Temperature sensor 400 may be connected to controller 220, and provide real-time temperature information for chamber 210. Controller 220, in conjunction with temperature sensor 400 and pressure regulator 250, can adjust the temperature within chamber 210 (and thus proximate to the module) and apply pressure to simulate actual weather conditions. Controller 220 may alter the applicable load gradually, or quickly, so as best to simulate natural weather conditions. For example, controller 220 may output a signal to pressure regulator 250, representative of a discrete or periodic applied pressure; controller 220 may receive temperature information via temperature sensor 400 and adjust the temperature within chamber 210 to one or more desired levels. Pressure regulator 250 may contain a pressure sensor configured to provide pressure information to controller 220, for determining a subsequent pressure to be applied to the photovoltaic module. System 20 may also include an accelerometer 410 in communication with controller 220 to determine formation of cracks within the photovoltaic module. Based on information received from accelerometer 410, controller 220 may calculate a threshold load capacity for the photovoltaic module. Pressure regulator 250, temperature sensor 400, and accelerometer 410 may be connected to controller 220 using any suitable means, including, for example, any suitable form of hardwire or wireless communication.

The embodiments described above are offered by way of illustration and example. It should be understood that the examples provided above may be altered in certain respects and still remain within the scope of the claims. It should be appreciated that, while the invention has been described with reference to the above preferred embodiments, other embodiments are within the scope of the claims.

What is claimed is:

1. A system for load testing a photovoltaic module, comprising
    a structure for positioning a photovoltaic module surface at a load test position; and
    a load test device proximate to the structure, comprising an array of pressure applicators and respective actuators, wherein the actuators are capable of moving the pressure applicators toward the load test position such that the pressure applicators can engage with the photovoltaic module surface.

2. The system of claim 1, wherein the actuators are capable of moving the respective pressure applicators away from the load test position.

3. The system of claim 1, wherein each of the pressure applicators comprises a suction cup.

4. The system of claim 1, wherein each of the pressure applicators comprises a pad.

5. The system of claim 1, wherein each of the actuators comprises a pneumatic actuator.

6. The system of claim 5, wherein each of the pneumatic actuators comprises an air cylinder.

7. The system of claim 1, wherein each of the actuators comprises a motor.

8. The system of claim 1, wherein each of the actuators comprises a hydraulic cylinder.

9. The system of claim 1, further comprising a controller capable of outputting a load signal to the load test device to apply pressure at the load test position.

10. The system of claim 9, wherein the pressure comprises positive pressure applied to push a photovoltaic module surface from the load test position in a direction away from the load test device.

11. The system of claim 9, wherein the pressure comprises negative pressure applied to pull a photovoltaic module surface from the load test position in a direction toward the load test device.

12. The system of claim 3, further comprising a vacuum pump connected to each of the suction cups to connect the suction cup to a photovoltaic module surface.

13. The system of claim 1, further comprising a load fail detector capable of detecting breakage in a photovoltaic module.

14. The system of claim 13, wherein the load fail detector comprises an accelerometer attached to a photovoltaic module.

15. A system for determining load capacity for a photovoltaic module, the system comprising:
a chamber configured to receive a photovoltaic module;
an array of air cylinders positioned proximate to the chamber;
a plurality of suction cups, each one of the plurality of suction cups connected to each air cylinder of the array of air cylinders;
a vacuum pump connected to each suction cup to allow the suction cup to be secured to a surface of a photovoltaic module;
an air pressure regulator in connection with the array of air cylinders, wherein each one of the array of air cylinders is connected to a common manifold to ensure a substantially even distribution of air pressure;
a controller in connection with the air pressure regulator, wherein the air pressure regulator is configured to apply pressure to a photovoltaic module received by the chamber.

16. The system of claim 15, wherein the controller is configured to output a load signal to the air pressure regulator, the load signal defining an amount of negative or positive pressure for the air pressure regulator to apply to a photovoltaic module via the array of air cylinders.

17. The system of claim 16, wherein the air pressure regulator is configured to adjust a negative or positive pressure on a photovoltaic module, upon receiving the load signal from the controller.

18. The system of claim 15, further comprising an accelerometer in connection with the controller, wherein the accelerometer is configured to determine formation of a crack in a photovoltaic module received by the chamber, and to output a threshold load signal to the controller, wherein the threshold load signal defines a maximum sustainable load for a photovoltaic module received by the chamber.

19. The system of claim 15, wherein the controller is configured to identify a threshold load capacity of a photovoltaic module received by the chamber.

20. The system of claim 15, further comprising a power supply in connection with the air pressure control regulator.

21. The system of claim 15, further comprising a temperature sensor in connection with the controller for determining a temperature within the chamber.

22. The system of claim 15, wherein the controller is configured to output a temperature adjustment signal, wherein the temperature adjustment signal defines a new chamber temperature.

23. The system of claim 15, wherein the controller comprises a temperature control device configured to increase or decrease a temperature within the chamber.

24. The system of claim 15, wherein the array of air cylinders is positioned within the chamber.

25. The system of claim 15, wherein the chamber is configured to receive a photovoltaic module on top of the array of air cylinders.

26. The system of claim 15, wherein the chamber comprises one or more clips for securing a photovoltaic module within the chamber.

27. A method for determining load capacity for a photovoltaic module, the method comprising:
positioning a photovoltaic module proximate to an array of air cylinders;
applying a positive or negative air pressure to the photovoltaic module via the array of air cylinders; and
identifying a threshold load capacity of the photovoltaic module, wherein the threshold load capacity defines a maximum sustainable quantity of applied positive or negative pressure for the photovoltaic module.

28. The method of claim 27, further comprising adjusting the applied positive or negative pressure.

29. The method of claim 27, wherein the step of applying a positive or negative pressure comprises applying positive air pressure to a surface of the photovoltaic module.

30. The method of claim 27, wherein the step of applying a positive or negative pressure comprises applying a suction force to a surface of the photovoltaic module.

31. The method of claim 27, further comprising setting a first temperature in the chamber.

32. The method of claim 31, wherein the first temperature is between about −20 degrees C. and about 140 degrees C.

33. The method of claim 31, further comprising adjusting the first temperature to a second temperature.

34. The method of claim 33, wherein the second temperature is between about −20 degrees C. and about 140 degrees C.

35. The method of claim 34, wherein the second temperature is between about −10 degrees C. and about 110 degrees C.

36. The method of claim 27, further comprising identifying a crack in the photovoltaic module caused by the applied positive or negative pressure.

37. The method of claim 27, wherein the identified threshold capacity corresponds to the applied positive or negative pressure that caused the crack in the photovoltaic module.

38. The system of claim 1, wherein each one of the array of pressure applicators and respective actuators are connected to a common manifold.

39. The system of claim 16, wherein the load signal is configured to apply a predetermined load for a fixed duration of time.

40. The system of claim 16, wherein the load signal is configured to periodically apply a predetermined load.

41. The system of claim 16, wherein the load signal is configured to gradually increase a load.

42. The method of claim 27, wherein applying the applied positive or negative air pressure further comprises applying a predetermined load for a fixed duration of time.

43. The method of claim 27, wherein applying the applied positive or negative air pressure further comprises periodically applying a predetermined load.

44. The method of claim 27, wherein applying the applied positive or negative air pressure further comprises gradually increasing an applied load.

* * * * *